United States Patent [19]

Rossey et al.

[11] Patent Number: 5,008,434
[45] Date of Patent: Apr. 16, 1991

[54] PROCESS FOR THE PREPARATION OF METHYL (+)-(2S,3S)-3-[(2-AMINOPHENYL)THIO]-2-HYDROXY-3-(4-METHOXYPHENYL)-PROPIONATES

[75] Inventors: Guy Rossey, Voisins le Bretonneux; Antonio Ugolini, Le Pecq; Isaac Chekroun, Pinay; Abkar Vartanian, Meulan; Alexander Wick, St Nom la Breteche, all of France

[73] Assignee: Synthelabo, Paris, France

[21] Appl. No.: 339,979

[22] Filed: Apr. 18, 1989

[30] Foreign Application Priority Data

Apr. 19, 1988 [FR] France .................. 88 05132

[51] Int. Cl.$^5$ .................. C07C 67/30; C07C 323/09
[52] U.S. Cl. .................. 560/17; 562/431
[58] Field of Search .................. 560/17; 562/431

[56] References Cited

U.S. PATENT DOCUMENTS 4,416,819 11/1983 Nagao et al. .................. 540/491

FOREIGN PATENT DOCUMENTS 158339 10/1985 European Pat. Off. .
158340 10/1985 European Pat. Off. .

OTHER PUBLICATIONS

Patent Abstracts of Japan, vol. 10, No. 339 (C-385) (2395), Nov. 15, 1986 & JP-A-61 145 160 (Nippon Chemiphar) 02-02-1986.
Patent Abstracts of Japan, vol. 10, No. 339 (C-385) (2395), Nov. 15, 1986 & JP-A-61 145 159 (Nippon Chemiphar) 02-02-1986.

Primary Examiner—Jose G. Dees
Assistant Examiner—Vera C. Clarke
Attorney, Agent, or Firm—Fleit, Jacobson, Cohn, Price, Holman & Stern

[57] ABSTRACT

A process for the preparation of a methyl (+)-(2S,3S)-3-[(2-aminophenyl)thio]-2-hydroxy-3-(4-methoxyphenyl)propionate of the formula (I):

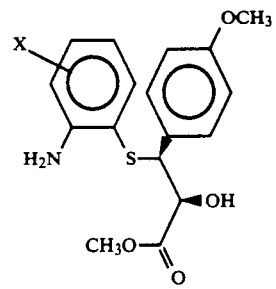

in which X denotes hydrogen or chlorine, which process comprises reacting a 2-aminothiophenol of formula (II):

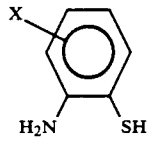

in which X is as defined above, with methyl (−)-(2R,3S)-2,3-epoxy-3-(4-methoxyphenyl)propionate, in a 1,2-dichloroethane solvent.

3 Claims, No Drawings

PROCESS FOR THE PREPARATION OF METHYL (+)-(2S,3S)-3-[(2-AMINOPHENYL)THIO]-2-HYDROXY-3-(4-METHOXYPHENYL)-PROPIONATES

The present application relates to a process for the preparation of a methyl (+)-(2S,3S)-3-[2-(aminophenyl)thio]2-hydroxy-3-(4-methoxyphenyl)propionate and to a propionate having (+)-(2S,3S) configuration.

These compounds may be used as intermediates in the stereospecific synthesis of diltiazem (DCI) and chlorinated derivatives thereof. They have the formula (I) given below in which X denotes hydrogen or chlorine.

The present invention provides a process for the preparation of a methyl (+)-(2S,3S)-3-[(2-aminophenyl)thio]-2-hydroxy-3-(4-methoxyphenyl)propionate of the formula (I):

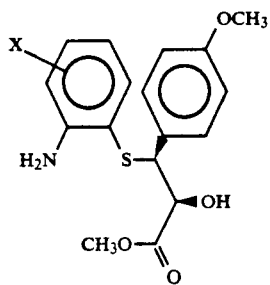

in which X denotes hydrogen or chlorine, which process comprises reacting a 2-aminothiophenol of formula (II): in which X is as defined above, with methyl (−)-(-2R,3S)2,3-epoxy-3-(4-methoxyphenyl)propionate, in a 1,2-dichloroethane solvent.

The process according to the invention is illustrated by the scheme below:

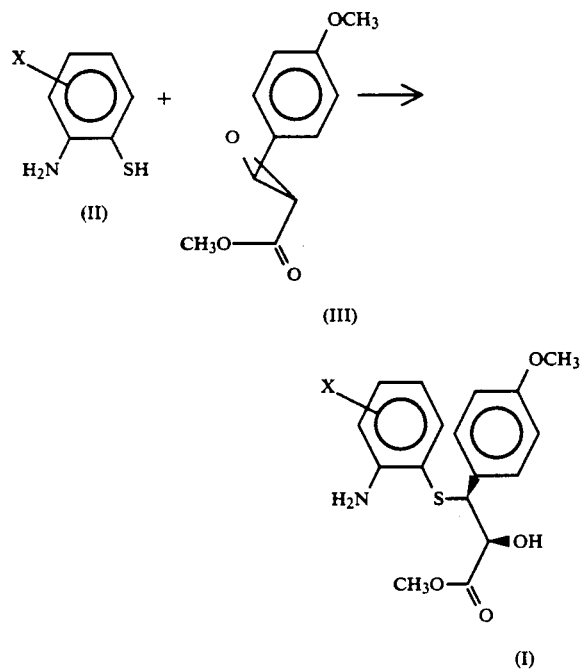

It consists in reacting a 2-aminothiophenol of formula (II), in which X is as defined above, with methyl (−)-(2R,3S)-3-(4-methoxyphenyl)glycidate of formula (III), preferably with heating and under an inert atmosphere.

The starting compounds for the reaction are described in the literature; the (−)-(2R,3S) isomer of the glycidate, in particular, is described in Japanese Patent Applications 145,159/1986, 145,160/1986 and 145,174/1986.

The principle of this reaction has been described many times in the literature, particularly in connection with processes where the racemic glycidate is involved, and where the final product is consequently a mixture of optical isomers.

The problem was to be able to synthesize an optically pure compound of formula (I), that is to say a compound having (2S,3S) configuration.

It is not sufficient to employ the (2R,3S) enantiomer of the glycidate, because a mixture of diastereoisomers, erythro and threo, is still obtained, in which the threo/erythro ratio is more or less advantageous, and from which the threo form must be isolated in a further step. In starting with the optically pure glycidate the whole difficulty consisted, therefore, in obtaining, by the action of 2-aminothiophenol, and in a high yield, the threo diastereoisomer of the aminoester having the desired relative stereochemistry.

In most cases, the known processes employ aromatic solvents such as toluene, xylene and ethylbenzene and result in threo/erythro ratios of little interest.

This is why an object of the present invention is to offer a process which can be employed on an industrial scale and yielding a good threo/erythro ratio, without this advantageous aspect being diminished by disadvantages such as, for example, lengthening of the reaction period or increase in the quantity of energy to be supplied.

This objective has been attained, in accordance with the invention, by virtue of the use of 1,2-dichloroethane as a solvent.

Another advantageous feature of the process of the invention relates to the fact that it is unnecessary to add a catalyst to the reaction in order to obtain high yields, in contrast to the known processes. This characteristic contributes to a further improvement in the purity of the final product.

Lastly, it should be noted that methyl 3-[(2-amino-5-chlorophenyl)thio]-2-hydroxy-3-(4-methoxyphenyl)-propionate, of (2S,3S) configuration, which corresponds to formula (I), is new and forms part of the invention.

The Examples which will follow further illustrate the invention.

EXAMPLE 1

Methyl (+)-2S,3S)-3-[(2-aminophenyl)thio]-2-hydroxy-3-(4-methoxyphenyl)propionate.

200 g of methyl (−)-(2R,3S)-2,3-epoxy-3-(4methoxyphenyl)propionate, 133 g of 2-aminothiophenol and 900 ml of 1,2-dichloroethane are introduced into a 2-l three-necked round-bottom flask, kept under nitrogen. The mixture is heated under reflux for 4 h 30 min and 400 ml of solvent are then removed by distillation. 500 ml of cyclohexane are added and the mixture is allowed to crystallize at ambient temperature for 2 h. It is then cooled to 10° C. for 1 h and filtered. The solid is washed with 200 ml of a 60/40 mixture of cyclohexane/dichloromethane and dried at 60° C. under vacuum for 12 h. 266.3 g of product are finally collected. Melting point: 110° C.

$[\alpha]_D^{20} = +294°$ (c = 0.5; MeOH).

EXAMPLE 2

Methyl (+)-(2S,3S)-3-[(2-amino-5-chlorophenyl)thio]-2-hydroxy-3-(4-methoxyphenyl)propionate.

1.5 g of methyl (−)-(2R,3S)-2,3-epoxy-3-(4methoxyphenyl)propionate, 11.5 ml of 1,2-dichloroethane and 1.18 g of 2-amino-5-chlorothiophenol are placed in a 50-ml round-bottom flask. The mixture is heated under reflux with stirring for 4 h 30 min. The reaction mixture is evaporated to dryness under vacuum, the residue is chromatographed on silica and concentrated. 1.4 g of product are obtained, are dissolved in 5 ml of hot ethyl acetate, and 10 ml of n-hexane are then added to the solution. The product crystallizes and then sets solid. It is left to stand in the refrigerator for 3 h. It is filtered off, washed with hexane and dried under vacuum. Melting point: 124-126° C.

$[\alpha]_D^{20} = +244°$ (c = 0.5; MeOH).

We claim:

1. A process for the preparation of a methyl (+)-(2S,3S)-3-[(2-aminophenyl)thio]-2-hydroxy-3(4-methoxyphenyl)propionate of the formula (I):

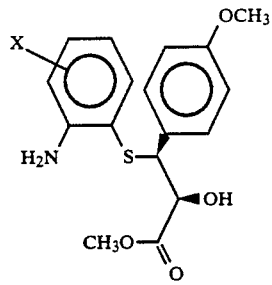

in which X denotes hydrogen or chlorine, which process comprises reacting a 2-aminothiophenol of the formula (II):

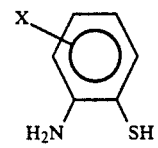

in which X is as defined above, with methyl (−)-(2R,3S)2,3-epoxy-3-(4-methoxyphenyl)propionate, in a 1,2-dichloroethane solvent, at reflux temperature and under an inert atmosphere.

2. A process according to claim 1, wherein the reaction is carried out in the absence of a catalyst.

3. Methyl(+)-(2S,3S)-3-[(2-amino-5-chlorophenyl)thio]-2-hydroxy-3-(4-methoxyphenyl)propionate.

* * * * *